US005529668A

United States Patent [19]

Hall

[11] Patent Number: 5,529,668
[45] Date of Patent: Jun. 25, 1996

[54] DETECTION OF POTENTIAL FOR CORROSION OF STEEL REINFORCED COMPOSITE PIPE

[75] Inventor: Sylvia C. Hall, Bell, Calif.

[73] Assignee: Ameron, Inc., Pasadena, Calif.

[21] Appl. No.: 345,569

[22] Filed: Nov. 28, 1994

[51] Int. Cl.⁶ ................................................. G01N 27/26
[52] U.S. Cl. ................ 205/776.5; 204/404; 340/605; 324/522; 324/555; 324/557; 324/750; 324/71.1; 324/71.2; 205/777
[58] Field of Search .................. 204/404, 153.11; 324/71.2, 71.1, 522, 750, 555, 557; 340/605

[56] References Cited

U.S. PATENT DOCUMENTS

| | | | |
|---|---|---|---|
| 4,101,827 | 7/1978 | Offner | 324/65 R |
| 4,110,739 | 8/1978 | Kidd | 340/605 |
| 4,351,364 | 9/1982 | Cocks | 138/133 |
| 4,357,573 | 11/1982 | Heuze | 324/54 |
| 4,365,191 | 12/1982 | Weldon et al. | 324/71 R |
| 4,390,836 | 6/1983 | Bruce et al. | 324/54 |
| 4,437,065 | 3/1984 | Woudstra | 324/425 |
| 4,543,525 | 9/1985 | Boryta et al. | 324/54 |
| 4,636,732 | 1/1987 | Willis | 324/425 |
| 4,687,996 | 8/1987 | Okazaki et al. | 324/436 |
| 4,703,255 | 10/1987 | Strommen | 204/153.11 |
| 4,719,407 | 1/1988 | Converse et al. | 324/546 |
| 4,755,757 | 7/1988 | Cooper | 324/557 |
| 4,771,246 | 9/1988 | Boryta et al. | 324/559 |
| 4,882,682 | 11/1989 | Takasuka et al. | 364/507 |
| 4,985,682 | 1/1991 | Boryta | 324/557 |
| 4,994,159 | 2/1991 | Agarwala et al. | 204/153.11 |
| 5,015,355 | 5/1991 | Schiessl | 204/404 |
| 5,214,387 | 5/1993 | Fenner | 324/557 |

*Primary Examiner*—Bruce F. Bell
*Attorney, Agent, or Firm*—Christie, Parker & Hale

[57] ABSTRACT

This method and apparatus detects the potential for corrosion of pipes fabricated out of conductive material embedded in non-conductive material, due to contact between a conductive medium foreign to the pipe and the conductive material embedded within the pipe wall. The electric potential between the foreign medium and the pipe conductive material is determined. The stability of the potential is then ascertained. If the potential does not vary beyond a predetermined range over a period of time, the potential is deemed stable and is indicative of contact between the foreign medium and the conductive material within the pipe, fostering corrosion. An unstable voltage indicates lack of electrical contact.

18 Claims, 1 Drawing Sheet

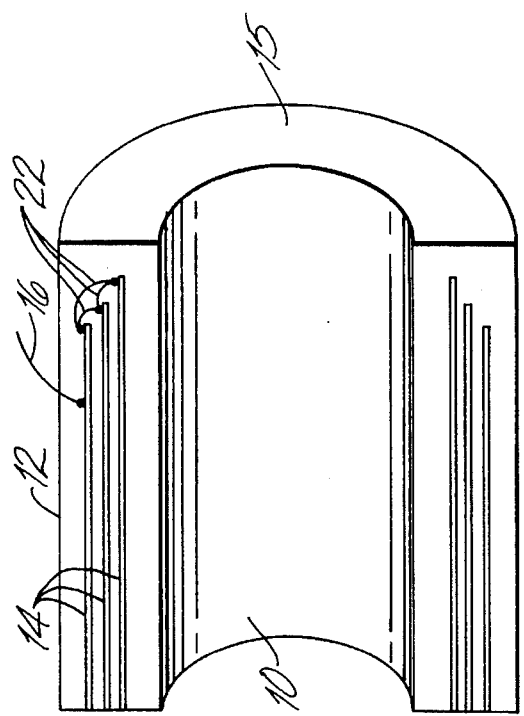
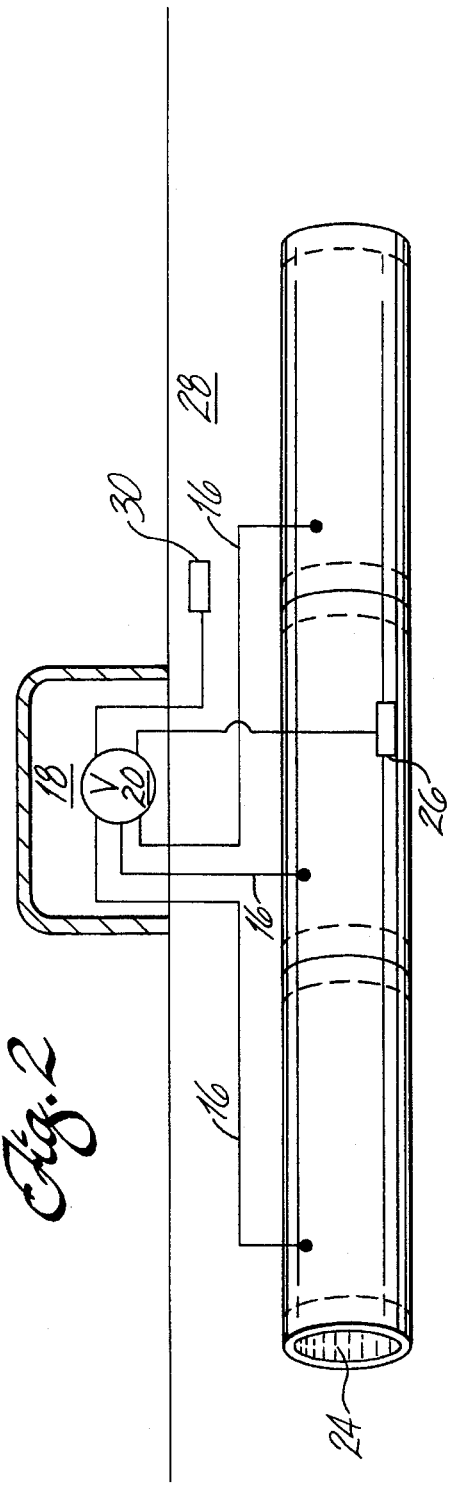

1

DETECTION OF POTENTIAL FOR CORROSION OF STEEL REINFORCED COMPOSITE PIPE

FIELD OF THE INVENTION

This invention relates to a technique for detection of the potential for corrosion of steel reinforced composite pipes due to contact between electrolytic media foreign to the pipes and the steel embedded within their walls. Broadly, this technique involves detecting the presence or absence of a stable potential between the steel and the foreign medium.

BACKGROUND OF THE INVENTION

High pressure conduits, such as oil and gas pipelines, have generally been constructed with conventional steel pipes. These pipelines are subjected to both internal and external pressures. Internal pressure is required to transport the fluids or gases within the pipeline. External pressure is created by the weight of soil or water on the pipeline when the pipeline is buried underground or submerged in water.

While steel pipes provide the requisite strength for withstanding the internal and external pressure, they have a high susceptibility to corrosion. A corrosive environment is fostered by contact between internal foreign media (e.g., the electrolytic liquids or gases being transported by the pipeline) and the steel, or by contact with external conductive foreign media and the steel. The external foreign media could be soil in cases where the pipe is buried underground, or sea water in cases where the pipe is submerged in an ocean, or water in cases where the pipe runs along sewer systems or is exposed to rain. Corrosion decreases the pipe's strength and may cause the pipe to leak or burst under pressure.

To overcome this disadvantage, steel reinforced composite pipes have been developed. These pipes have a wall of steel coated with a polymeric material, or of steel embedded in a fiber reinforced composite, such as a fiberglass-resin system. The coating or resin system protects the steel from corrosion by shielding it from any contact with the foreign media. One example of steel reinforced composite pipe is disclosed in the Cocks U.S. Pat. No. 4,351,364, the subject matter of which is hereby incorporated by reference. The pipe disclosed has a structural wall section sandwiched between inner and outer linings. The linings are resin-rich layers reinforced with glass or other fibers. The structural wall section is made of three or more structural steel reinforcing layers coated with structural epoxy resin. The individual layers of the pipe are successively built up, one upon the other, on a mandrel or pipe winding machine. Each lining layer is formed by helically winding resin wetted fiber rovings. Each steel layer is formed by helically winding a steel strip coated with resin.

Since most of these pipelines are buried or submerged, visual inspections, of the outer surface at least, is a difficult and expensive proposition. The soil burying the pipe would have to be excavated in cases where the pipe is buried underground. In cases where the pipe is submerged in water, divers may have to do the visual inspection. Visual inspection within a pipeline poses obvious difficulties.

Even if visual inspections were possible, the onset of steel corrosion may not be visually detectable, since the steel layers are coated or covered with a fiber-resin system. In many cases, the corrosion becomes visually detectable only when it has progressed far enough to affect the protective layers. It is possible that the pipes will leak or burst prior to the corrosion ever becoming visually detectable. It is imperative, therefore, that any contact of the steel with a corrosion fostering foreign medium be detected so that timely action is taken to prevent the corrosion onset. A system capable of detecting such contact would reduce pipeline inspection costs and reduce pipeline failures. To be successful, such a system must be capable of functioning without interfering with the pipeline operation. In other words, the pipeline operation should not have to be stopped every time a pipe section needs to be inspected. Otherwise, the costs involved in stopping the pipeline operation may make such a detection system economically infeasible.

DESCRIPTION OF THE RELATED ART

Various systems have been disclosed for the detection of leakage or corrosion of a pipe or vessel, none of which disclose the present invention. The Kidd U.S. Pat. No. 4,110,739, discloses a system for detecting leaks in laminated vessels or pipes filled with an electrolytic fluid. The pipe or vessel contains a conductive layer laminated between a fiberglass reinforced polyester outer wall and a corrosion-resistant thermoplastic inner wall. Detection of fluids leaking from inside the pipe is predicated on establishing an electrical circuit connecting four components: an electrically conductive probe; a battery connected to the probe; an alarm connected to the battery; and a wire connecting the alarm to the conductive layer of the pipe. In operation, the circuit is closed and a leak is detected by the alarm when a break in the inner wall of the pipe allows electrolytic fluid to establish a conductive path between an end of the probe and the conductive layer of the pipe. This disclosure is limited to the detection of leakage through the pipe inner protective layer. A method for detecting leakage through the pipe outer protective layer is not disclosed.

The Offner U.S. Pat. No. 4,101,827, discloses a method for locating leaks in pipe, made from an electrically insulating material, which is buried in an electrically conductive medium (e.g., underground). The pipe is filled with an electrically conductive fluid (e.g., tap water). An electric current is passed through the fluid, establishing a voltage gradient along the length of the fluid in the pipe. The voltage gradient is analyzed to determine the location of the leak. In one embodiment, one terminal of a voltmeter is connected to ground and the other terminal is connected to the bare end of an insulated conductor which is drawn though the pipe to measure the voltage gradient. In another embodiment, a voltage source is connected to the fluid at opposite ends of the pipe to establish a voltage gradient for the distance between those ends. The voltage drop between the fluid at one end of the pipe and the ground is then measured and the distance from that end to a leak point is established by a relationship between these two voltages and distances. This system, unlike the present invention, requires the use of a current source.

The Fenner U.S. Pat. No. 5,214,387, discloses a detector for detecting permeation of liquids through the walls of fiber reinforced composite vessels. The detector is equipped with at least two and as many as four electric sensors which are connected to form an electrical circuit. One sensor takes the form of a wet common reference point by penetrating into the interior of the vessel. The others are dry reference points which are embedded at various depths within the vessel wall. An ammeter is used to measure the resistance between the electrode penetrating the liquid in the interior of the vessel and the dry electrodes. Permeation of the liquid into the vessel wall is denoted by the measurement of a low resistance. This technique is limited to the detection of permeation of liquid into the vessel walls at the location of the sensors. If a leak occurs in a location different from the location of a sensor it would not be detected. The present technique, however, allows for the detection of leaks through the composite layers occurring anywhere along the pipe. Furthermore, Fenner employs galvanometers in leak detection, while the present invention detects leakage based on the stability of electric potentials measured using millivolt sensors.

The prior art does not disclose the present invention. While, it reveals some methods and apparatuses for detecting leaks through pipe or vessel walls, none of the prior art reveals the method and apparatus of the present invention which are based on the stability of millivolt electric potential measurements.

BRIEF SUMMARY OF THE INVENTION

A method and apparatus are used for detecting contact, which may foster corrosion, between two or more conductive media insulated from each other by non-conductive media, by determining the stability of the electric potential between the insulated conductive media whose contact is being detected. Variations of the potential within a predetermined range over a period of time, denotes lack of contact between the insulated conductive media. On the other hand, a stable, unchanging potential indicates that the electrolyte has made contact with the steel with the potential for corrosion.

BRIEF DESCRIPTION OF THE DRAWINGS

FIG. 1 is a cross-sectional view of a steel-reinforced composite pipe section. The view is not in scale.

FIG. 2 is a schematic drawing of a subterranean high pressure pipeline composed of steel reinforced composite pipe sections made of steel embedded in fiberglass-resin. Also depicted in the drawing is the system for detecting contact between the steel within the pipe and media foreign to the pipe. The drawing is not in scale.

DETAILED DESCRIPTION

Steel reinforced composite pipes are likely to be used in pipelines which carry crude oil under pressure. These pipelines are typically buried underground. Contact of the steel with either the crude oil or soil leads to corrosion. Crude oil, unlike refined oil, is both conductive and corrosive because it contains electrolytic matter such as brine. To protect the steel from such corrosion-leading contact, these pipes have a steel structural wall section sandwiched between inner 10 and outer 12 linings. The linings are resin-rich layers reinforced with glass or other fibers and are therefore non-conductive. The structural wall section is made of three or more structural steel reinforcing layers 14 coated with a structural epoxy resin. The individual layers of the pipe are successively built up, one upon the other, on a mandrel or pipe winding machine. Each lining layer is formed by helically winding resin wetted fiber rovings. Each steel layer is formed by helically winding a steel strip coated with resin.

A preferred embodiment of the present invention determines the electric potential between the steel embedded within the pipe and a foreign electrolytic medium flowing inside the pipe, as well as between the steel embedded within the pipe and a foreign medium outside the pipe, using a sensitive voltmeter.

A lead 16 is connected to a steel layer of the pipe and protrudes through the external pipe lining 12. Several techniques can be used to facilitate this connection. In one technique, the lead is connected to the pipe steel layer during the fabrication process. In other words, the lead is "manufactured" with the pipe. Another technique makes an opening through the pipe outer liner to accommodate the lead. The lead is inserted through the opening until it makes contact with the steel layer. The opening-lead interface is then sealed.

The steel layers 14 do not span the whole length of the pipes. Rather, they stop short of the pipe ends 15, as shown in FIG. 1. Therefore, there is no continuous electrical path between each pipe on a pipeline. Hence, a lead 16 must be connected to each individual pipe in the pipeline. The leads run along the exterior surface of the pipeline in the trench and surface at appropriate intervals denoted as test stations 18. At each test station, these leads are connected to a first terminal of a voltmeter 20. These voltmeters should have greater than 10 megohm input impedance, otherwise, the steel may be polarized by the voltmeter, affecting the electric potential measurements.

To establish an electrical path between lead 16 and the steel layers to which the lead is not connected, wires 22 are used interconnecting all the layers. When leakage through a protective lining occurs, the foreign media contacts either the outermost or innermost steel layer. Since in most situations the lead 16 is connected to the outermost steel layer, a connection between only the outermost and innermost steel layers may be sufficient. Connections using wires 22 may not be needed in steel reinforced composite pipes of the type disclosed by the Cocks patent. It has been found that the steel layers in the Cocks-type pipe are in electrical contact with each other even though they are coated with layers of resin. This is so because during fabrication the resin coating spreads thinly, and apparently non-uniformly, creating openings which allow for contact between the steel layers.

To determine if the transported fluid (electrolyte) 24 being carried by the pipe has made contact with the innermost steel layer of a pipe, the second terminal of the voltmeter is connected to an electrode 26 or a piece of metal which is immersed in the fluid travelling within the pipe. The piece of metal can be, for example, a valve or other fitting that is in contact with the fluid but insulated from the steel layers within the pipe wall. An occasional electrode is all that is required along a pipeline. It is not considered necessary to have an electrode for each piece of pipe as long as the foreign medium is reasonably conductive.

If the fluid is making contact with the innermost steel layer, a complete circuit is formed and a stable millivolt electric potential is registered on the voltmeter. On the other hand, if the inner non-conductive layer is intact and there is no electrical contact between the liquid in the pipe and the steel embedded in the wall of the pipe, the electric potential between the two is unstable. This ground potential varies with time and can be seen to be unstable. A leak through the inner layer effectively shorts the steel to the liquid and stabilizes the electric potential. The potential may or may not be zero depending on the electrolytic action, but at least it remains stable over short time intervals. The stability of voltage can be observed regardless of measurable current flow between the liquid and the steel.

To determine if the soil 28 burying the pipeline has made contact with the outermost steel layer of the pipe, the second terminal of the voltmeter is connected to an electrode 30 or a piece of metal submerged in the surrounding soil. The metal could be any conductive structure, such as, a nearby steel pipeline, a galvanized chain link fence post, a valve, or a steel stake driven into the soil. If the soil is making electrical contact with the outermost steel layer, a complete circuit is formed and a stable millivolt electric potential is registered on the voltmeter. An unstable potential indicates absence of electrical contact. Testing is similar for a submerged pipeline where one lead of the voltmeter is connected to a metal submerged in the surrounding water.

Hence, depending on the connection of the second voltmeter lead, a stable potential reading is indicative of contact of either the soil or the transported fluid and the steel layers within the pipe wall, denoting the potential for corrosion. Stable potentials are those which do not change by more than one millivolt over a predetermined time period. For this particular type of pipe, the appropriate time period recommended is approximately ten seconds or less, with one second being sufficient.

The stability of the electric potential can be readily observed visually with a high impedance voltmeter (e.g., 10 megohms) where less than one millivolt change is indicated on a digital voltmeter and may be observed on an analog meter with one millivolt being an analog appreciable fraction of full scale. When there is electrical contact, the readings (or needle) are unchanging. When the linings are intact and there is no electrical contact, varying voltage readings are easily seen. Only a few seconds are sufficient for distinguishing between stable and unstable voltages.

This technique can be used to check the pipes before they are installed on the pipeline or to check the pipes after they are installed on the pipeline but before they become operational. Furthermore, the technique can be used to perform inspections as part of an on-going periodic maintenance program. It can also be part of an automated system that remotely monitors the entire pipeline from a central station. Voltmeters at each test station can measure the potentials for each pipe assigned to that station. The measurements are then fed to a computer which evaluates the stability of the measured potentials for each pipe and determines if there is contact of the steel layers with either the soil or transported fluid, fostering corrosion. If there is such contact, a code identifying the pipe affected is passed to a central station so that remedying actions can be taken. In the alternative, all the voltmeter readings may be passed directly to the central station where a central computer evaluates the readings from each pipe in the pipeline and determines if potentially corrosive contact has occurred. Since these pipelines are typically many miles in length, it may be beneficial to beam the information from the test stations to a satellite which in turn will beam it to the central station.

Once the potential for corrosion is detected the affected pipes can be repaired or replaced. The timing for the repair or replacement of the affected pipes may depend on the time period between the onset of corrosion and failure due to such corrosion. The pipe disclosed by the Cocks patent is designed to withstand at least a year of corrosion formation before failure. In other words, from the onset of corrosion, this pipe can safely operate a full year in a corrosive environment. Therefore, if the onset of corrosion is detected immediately, no action to repair or replace the pipe is required for a year. Furthermore, this critical time period between the onset of corrosion and failure can be used to set inspection intervals. For example, if pipe has a critical time period of one year, the pipe can be inspected (monitored for the potential for corrosion) once a year. However, if monitored only once a year, the pipe should be repaired or replaced promptly since the actual time of corrosion onset would be unknown.

Although the described embodiment is specific to steel reinforced composite pipes, the method can just as easily be applied to any pipe or vessel that is fabricated from conductive materials or layers of material embedded in non-conductive materials.

It should be noted that the terms "conductive material" and "conductive medium" as used in this specification refer to material and media with any degree of conductivity (e.g., semi-conductive material). Even a very low conductivity material like crude oil is sufficient for shorting to the steel and producing stable voltages.

What is claimed is:

1. A method for detecting potentially corrosion-producing contact between two or more conductive media insulated from each other by non-conductive media, comprising the steps of:

determining an electric potential between the insulated conductive media as a function of time;

ascertaining whether variations of the potential, over a period of time, are greater or less than a set range; and repairing any corrosion damage or replacing any corroded conductive media in the event the variations are less than the set range.

2. A method for detecting the potential for corrosion in steel reinforced composite pipes, fabricated out of steel embedded in fiber reinforced composite, due to contact between a conductive medium foreign to the pipe and the steel, comprising the steps of:

connecting measuring means for measuring an electric potential as a function of time between the steel embedded within the wall of the pipe and the conductive foreign medium;

measuring an electric potential as function of time between the steel embedded within the wall of the pipe and the conductive foreign medium;

determining whether variations of the electric potential as a function of time are greater or less than a set range; and repairing or replacing the pipe in the event the variations are less than the set range.

3. A method as recited in claim 2, wherein the set range of electric potential variation is smaller than a millivolt.

4. A method as recited in claim 2, wherein the step of connecting the measuring means comprises the steps of:

connecting a first lead of a high input impedance voltmeter to the steel within the pipe; and connecting a second lead of the voltmeter to the foreign medium.

5. A method as recited in claim 4, wherein the step of connecting the first lead of the voltmeter to the steel within the pipe comprises the step of connecting a lead to the steel during the pipe manufacturing process so that the lead is embedded in the fiber reinforced composite and protrudes through the pipe's outer surface.

6. A method as recited in claim 4, wherein the step of connecting the first lead of the voltmeter to the steel within the pipe comprises the steps of:

creating an opening through the pipe's outer composite layer to the steel within the pipe;

inserting a lead through the opening so that it makes electrical contact with the steel; and sealing the opening-lead interface to secure the lead in place and to prevent any foreign media from entering the opening.

7. A method as recited in claim 4, wherein the steel comprises multiple layers of steel sheet within the fiber reinforced composite, and wherein the step of connecting a first lead of a high input impedance voltmeter to the steel within the pipe comprises the steps of:

connecting the first lead of the voltmeter to a steel layer; and connecting at least a portion of the steel layers to each other.

8. A method as recited in claim 4, wherein the step of connecting the second lead to the foreign medium comprises the step of connecting the second lead to an electrode, valve or other conductive intrusion within the pipe which is exposed to the carried foreign medium but not to the steel within the pipe wall.

9. A method as recited in claim 4, wherein the step of connecting the second lead to the foreign medium comprises the step of connecting the second lead to any foreign metallic or other conductive structure, embedded in soil, which is not in electrical contact with the steel within the pipe wall.

10. An apparatus for detecting contact between two or more conductive media insulated from each other by non-conductive media, comprising:

means for determining an electric potential between the insulated conductive media; and means for ascertaining whether variations of the electric potential, during a period of time, are less than a set range.

11. An apparatus for detecting the potential for corrosion in steel reinforced composite pipes, fabricated out of steel embedded in fiber reinforced composite, due to contact between a conductive medium foreign to the pipe and the steel, comprising:

means for establishing an electrical contact with the steel and an electrical contact with the foreign medium;

means for determining an electric potential between the steel and the foreign medium; and means for ascertaining whether variations of the electric potential, during a period of time, are less than a set range.

12. An apparatus as recited in claim 11, wherein the means for establishing electrical contact with the steel in the pipe comprises a lead connected to the steel, embedded within the fiber reinforced composite and protruding through the pipe's outer surface.

13. An apparatus as recited in claim 11, wherein the means for establishing electrical contact with the steel in the pipe comprises a lead which makes electrical contact with the steel within the pipe through an opening on the pipe's fiber reinforced composite outer surface.

14. An apparatus as recited in claim 11, wherein the means for determining the electric potential comprises a high input impedance voltmeter and further comprising:

means for connecting a first lead of the voltmeter to the steel within the pipe; and means for connecting a second lead of the voltmeter to the foreign medium.

15. An apparatus as recited in claim 14, wherein the voltmeter is sensitive to voltage variations of less than one millivolt.

16. An apparatus as recited in claim 14, wherein the steel comprises multiple layers of steel sheet within the fiber reinforced composite, further comprising:

means for connecting the first lead of the voltmeter to an outermost steel layer; and means for providing a conductive electrical path between all steel layers.

17. An apparatus as recited in claim 14, wherein the foreign medium comprises an electrolytic fluid carried by the pipe, further comprising:

means for connecting the second lead of the voltmeter to an electrode, valve or other conductive intrusion within the pipe which is exposed to the carried fluid and which is not in electrical contact with the steel within the pipe wall.

18. An apparatus as recited in claim 14, wherein the foreign medium comprises soil, further comprising:

means of connecting the second lead of the voltmeter to an electrode, or any foreign metallic or other conductive structure, embedded in soil, which is not in electrical contact with the steel within the pipe wall.

* * * * *